US00PP36263P2

(12) United States Plant Patent
Rose

(10) Patent No.: US PP36,263 P2
(45) Date of Patent: Nov. 26, 2024

(54) BLUEBERRY PLANT NAMED 'LB-30'

(50) Latin Name: *Vaccinium corymbosum*
Varietal Denomination: LB-30

(71) Applicant: Samuel Steele Rose, Ivanhoe, NC (US)

(72) Inventor: Samuel Steele Rose, Ivanhoe, NC (US)

( * ) Notice: Subject to any disclaimer, the term of this patent is extended or adjusted under 35 U.S.C. 154(b) by 0 days.

(21) Appl. No.: 18/586,498

(22) Filed: Feb. 25, 2024

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./157
See application file for complete search history.

(56) References Cited

U.S. PATENT DOCUMENTS

PP32,184 P2 * 9/2020 Brazelton ..... A01H 6/368 Plt./157

* cited by examiner

*Primary Examiner* — Karen M Redden
*Assistant Examiner* — Zachariah Allan Kay
(74) *Attorney, Agent, or Firm* — C. Anne Whealy

(57) ABSTRACT

A new and distinct cultivar of Blueberry plant named 'LB-30', characterized by its upright and bushy plant habit; vigorous growth habit and rapid growth rate; freely branching habit; relatively late ripening which reduces late season freeze damage; freely flowering habit with relatively high fruit yield; large fruits that are spherical and uniform in size; sweet fruit taste; firm fruit texture; resistance to splitting; and good storage and fruit postharvest longevity.

2 Drawing Sheets

Figure 1:
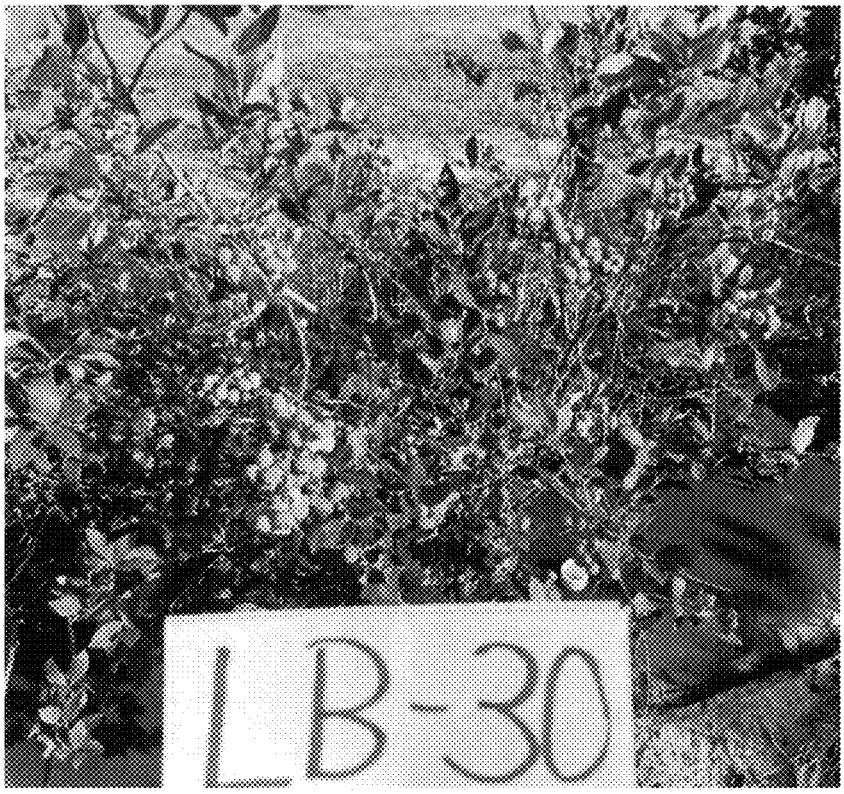

Botanical designation: *Vaccinium corymbosum.*
Cultivar denomination: 'LB-30'.

STATEMENT REGARDING PRIOR DISCLOSURES BY INVENTOR/APPLICANT

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor/Applicant. Inventor/Applicant claim a prior art exception under 35 U.S.C. 102(b)(1) for disclosure and/or sales prior to the filing date but less than one year prior to the effective filing date.

BACKGROUND OF THE INVENTION

The present Invention relates to a new and distinct cultivar of Blueberry plant, commonly referred to as a Southern Highbush Blueberry, botanically known as *Vaccinium corymbosum* and hereinafter referred to by the name 'LB-30'.

The new Blueberry plant is a product of a planned breeding program conducted by the Inventor in Ivanhoe, North Carolina. The objective of the breeding program was to develop new vigorous Blueberry plants with large fruits and good fruit quality, productivity, uniformity and postproduction longevity.

The new Blueberry plant originated from an open-pollination in 2015 in Ivanhoe, North Carolina by the Inventor of an unidentified selection of *Vaccinium corymbosum*, not patented as the female, or seed, parent with an unknown selection of *Vaccinium corymbosum*, not patented, as the male, or pollen, parent. The new Blueberry plant was discovered and selected by the Inventor as a single plant from within the progeny of the stated open-pollination in a controlled outdoor nursery environment in Ivanhoe, North Carolina in 2015.

Asexual reproduction of the new Blueberry plant by softwood cuttings in a controlled environment at Ivanhoe, North Carolina since 2015 has shown that the unique features of this new Blueberry plant are stable and reproduced true to type in successive generations of asexual reproduction.

SUMMARY OF THE INVENTION

Plants of the new Blueberry have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'LB-30'. These characteristics in combination distinguish 'LB-30' as a new and distinct Blueberry plant:

1. Upright and bushy plant habit.
2. Vigorous growth habit and rapid growth rate.
3. Freely branching habit.
4. Relatively late flowering which reduces late season freeze damage.
5. Freely flowering habit with relatively high fruit yield.
6. Fruit can be easily harvested by hand or machine.
7. Large fruits are spherical and uniform in size.
8. Sweet fruit taste.
9. Firm fruit texture; resists splitting.
10. Good storage and fruit postharvest longevity.

Plants of the new Blueberry differ primarily from plants of the unidentified female parent selection in the following characteristics:

1. Plants of the new Blueberry are more vigorous than the female parent selection.
2. Fruits of plants of the new Blueberry remain on the plant longer than fruits of plants of the female parent selection.

Plants of the new Blueberry can be compared to plants of *Vaccinium corymbosum* 'Legacy', not patented. In side-by-side comparisons, plants of the new Blueberry differ from plants of 'Legacy' in the following characteristics:

1. Plants of the new Blueberry are not as outwardly spreading as plants of 'Legacy'.
2. Leaves of plants of the new Blueberry are lighter green in color than leaves of plants of 'Legacy'.
3. Plants of the new Blueberry are not as freely flowering as plants of 'Legacy'.
4. Fruits of plants of the new Blueberry are darker blue in color than fruits of plants of 'Legacy'.

BRIEF DESCRIPTION OF THE PHOTOGRAPHS

The accompanying colored photographs illustrate the appearance of the new Blueberry plant showing the colors as true as it is reasonably possible to obtain in colored reproductions of this type. Colors in the photographs may differ slightly from the color values cited in the detailed botanical description which accurately describe the colors of the new Blueberry plant.

The photograph on the first sheet (FIG. 1) is a side perspective view of a typical fruiting plant of 'LB-30'.

Figure 2:
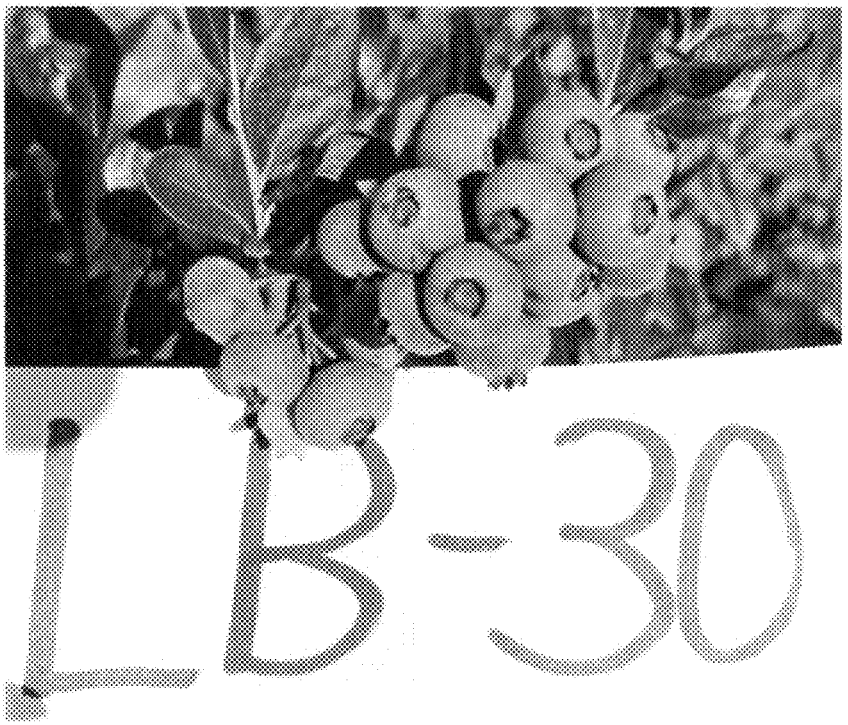

The photograph on the second sheet (FIG. 2) is a close-up view of typical fruits of 'LB-30' on the plant.

DETAILED BOTANICAL DESCRIPTION

The aforementioned photographs, following observations and measurements describe plants grown during the spring, summer and autumn in ground beds in an outdoor nursery in Ivanhoe, North Carolina and under typical cultural practices of Blueberry plant production. During the production of the plants, day temperatures averaged 27.7° C. and night temperatures averaged 10° C. Plants were two years old when the photographs and description were taken. In the following description, color references are made to The Royal Horticultural Society Colour Chart, 2019 Edition, except where general terms of ordinary dictionary significance are used.

Botanical classification: *Vaccinium corymbosum* 'LB-30'.

Parentage:

*Female, or seed, parent*.—Unidentified selection of *Vaccinium corymbosum*, not patented.

*Male, or pollen, parent*.—Unknown selection of *Vaccinium corymbosum*, not patented.

Propagation:

*Type*.—By soft wood cuttings.

*Time to initiate roots, summer*.—About four to five weeks at temperatures about 27° C.

*Time to produce a rooted young plant, summer*.—About six to eight weeks at temperatures about 27° C.

*Root description*.—Fine in thickness, fibrous, typically close to 163A in color; actual color of the roots is dependent on substrate composition, water quality, fertilizer type and formulation, substrate temperature and physiological age of roots.

*Rooting habit*.—Freely branching; medium density.

Plant description:

*Plant and growth habit*.—Upright and bushy plant habit; vigorous growth habit and rapid growth rate; plants produce fruit on one- year old shoots only.

*Plant height*.—About 150 cm.

*Plant diameter*.—About 81 cm.

Branch description:

*Quantity per plant*.—Freely branching habit with about four primary branches each primary branch with about five secondary branches.

*Length*.—About 38 cm.

*Diameter*.—About 5 mm.

*Internode length*.—About 2.5 cm.

*Strength*.—Strong.

*Aspect*.—About 30 to 45 degrees From vertical.

*Texture and luster*.—Smooth, glabrous; semi-glossy.

*Color, developing*.—Close to 145B.

*Color, developed*.—Close to 145A; if woody, close to 196C.

Leaf description:

*Arrangement*.—Alternate; simple.

*Length*.—About 4.5 cm to 7 cm.

*Width*.—About 2.1 cm to 3.5 cm.

*Shape*.—Elliptical.

*Apex*.—Acute, pointed.

*Base*.—Tapering, cuneate; asymmetrical.

*Margin*.—Entire, not lobed.

*Texture and luster, upper surface*.—Smooth, glabrous; dull, waxy.

*Texture and luster, lower surface*.—Prominent mid-vein, glabrous; semi-glossy, waxy.

*Venation*.—Pinnate and reticulate.

*Color*.—Developing leaves, upper surface: Close to N144B. Developing leaves, lower surface: Close to 145C. Fully expanded leaves, upper surface: Close to 146A; venation, close to 145B. Fully expanded leaves, lower surface: Close to 147C; venation, close to 145C.

*Petioles*.—Length: About 3 mm to 5 mm. Diameter: About 1 mm. Strength: Moderately strong. Texture and luster, upper and lower surfaces: Smooth, glabrous; semi-glossy. Color, upper surface: Close to 180B. Color, lower surface: Close to 150B.

Flower description:

*Flower form and flowering habit*.—Single urceolate-shaped flowers arranged in racemes; freely flowering with about four to six flowers per inflorescence and about 3,500 to 4,500 flowers developing per plant during the flowering season; flowers face mostly outwardly; flowers not persistent.

*Fragrance*.—Slightly fragrant, not distinct.

*Natural flowering season*.—In Ivanhoe, North Carolina, plants typically flower from mid-March to mid-May; relatively late flowering is beneficial in reducing late season freeze damage.

*Flower buds*.—Length: About 5 mm. Diameter: About 3 mm. Shape: Ovoid. Texture and luster: Smooth, glabrous; semi-glossy. Color: Close to 178B.

*Inflorescence height*.—About 2.5 cm.

*Inflorescence diameter*.—About 2 cm.

*Flower diameter*.—About 8 mm by 11 mm.

*Flower depth* (*height*).—About 1 cm.

*Petals*.—Arrangement: Five petals, fused. Length: About 1 cm. Shape: Urceolate. Apex: Cuspidate.

Margin, distal free part: Entire. Texture and luster, upper and lower surfaces: Smooth, glabrous; matte. Color: When opening, upper and lower surfaces: Close to 155D. Fully opened, upper and lower surfaces: Close to 155D; venation, close to 155D.

*Sepals*.—Arrangement: Five sepals, fused. Length: About 4 mm. Width: About 5 mm. Shape: Roughly deltoid. Apex: Acute. Margin, free part: Entire. Texture and luster, upper surface: Smooth, glabrous; semi- glossy. Texture and luster, lower surface: Smooth, glabrous; matte. Color, upper surface: Close to 150B. Color, lower surface: Close to 150C.

*Peduncles*.—Length: About 1.2 cm. Diameter: About 1.2 mm. Strength: Strong. Texture and luster: Smooth, glabrous; matte. Color: Close to 144C.

*Pedicels* (*flowers and fruits*).—Length: About 4.3 mm. Diameter: About 1 mm. Strength: Strong. Texture and luster: Smooth, glabrous; matte. Color: Close to 144C?.

*Reproductive organs*.—Stamens: Quantity per flower: About ten. Filament length: About 2 mm. Filament color: Close to 154C. Anther size: About 0.3 mm by 2 mm. Anther shape: Oblong. Anther color: Close to 163A. Pollen amount: Scarce. Pollen color: Close to 5D. Pistils: Quantity per flower: One. Pistil length: About 1 cm. Stigma diameter: About 0.4 mm. Stigma shape: Rounded. Stigma color: Close to 151C. Style length: About 9.75 mm. Style color: Close to 151C. Ovary color: Close to 144B.

*Fruits*.—Type: Berry; sepals, erect. Quantity: One per flower; about 4.99 kilograms of fruits are formed on one-year old plants. Time to ripening: Depending on temperatures, about one to two weeks. Keeping quality: Good postproduction longevity, about three to four weeks. Size: About 1.4 cm by 1.75 cm. Diameter of calyx basin: About 5 mm. Depth of calyx basin: About 0.5 mm. Weight: About 2.13 g. Shape: Roughly spherical. Firmness: Firm; resistant to splitting; about 238 g/mm. Texture and luster: Smooth, glabrous; somewhat glossy. Flesh color: Close to 157B. Skin color, developing, with waxy bloom: Close to 144C. Skin color, developing, without waxy bloom: Close to 144D. Skin color, developed, with waxy bloom: Close to 98D. Skin color, developed, without waxy bloom: Close to 202A. Taste: Sweet, slightly herbal; brix, close to 9.8%; medium acidity.

*Seeds*.—Quantity: About 13 to 16 per berry. Length: About 1.9 mm. Diameter: About 0.8 mm. Texture and luster: Smooth, glabrous; matte. Color: Close to N167B.

Pathogen & pest resistance: To date, plants of the new Blueberry have been observed to be resistant to pathogens and pests common to Blueberry plants.

Temperature tolerance: Plants of the new Blueberry have been observed to tolerate temperatures ranging from about −9.4° C. to about 37.2° C. and to be suitable for USDA Hardiness Zone 8A.

It is claimed:

1. A new and distinct Blueberry plant named 'LB-30' as herein illustrated and described.

* * * * *